United States Patent [19]
Thiele

[11] Patent Number: 5,620,935
[45] Date of Patent: Apr. 15, 1997

[54] METHOD FOR THE REGENERATION OF A CATALYST

[75] Inventor: Georg Thiele, Hanau, Germany

[73] Assignee: Degussa Aktiengesellschaft, Frankfurt am Main, Germany

[21] Appl. No.: 664,010

[22] Filed: Jun. 14, 1996

[30] Foreign Application Priority Data

Aug. 1, 1995 [DE] Germany .................. 195 28 220.5

[51] Int. Cl.$^6$ .................. B01J 38/48; C07D 301/12
[52] U.S. Cl. .................. 502/22; 502/20; 549/531; 585/365; 585/533; 585/526; 585/644; 585/529
[58] Field of Search .................. 549/531; 585/365, 585/533, 526, 644, 529; 502/20, 22

[56] References Cited

U.S. PATENT DOCUMENTS 5,374,747  12/1994  Saxton .................. 549/531

FOREIGN PATENT DOCUMENTS 0659479  6/1995  European Pat. Off. .

*Primary Examiner*—Glenn A. Caldarola
*Assistant Examiner*—Tanaga A. Boozer
*Attorney, Agent, or Firm*—Beveridge, DeGrandi, Weilacher & Young, L.L.P.

[57] ABSTRACT

Zeolites containing titanium atoms used as catalyst for the preparation of epoxides from olefins and hydrogen peroxide are regenerated by treating the spent catalyst with hydrogen peroxide in the absence of olefins and the regenerated catalyst is again used for the epoxidation.

21 Claims, No Drawings

METHOD FOR THE REGENERATION OF A CATALYST

INTRODUCTION AND BACKGROUND

The present invention relates to a method for the regeneration of a catalyst, in particular a zeolite containing titanium atoms which is used as a catalyst for the preparation of epoxides from olefins and hydrogen peroxide.

The preparation of epoxides from olefins by converting the olefin to the epoxide by means of hydrogen peroxide in the presence of a zeolite containing titanium atoms as catalyst is known (EP-A 0 100 119). M. G. Clerici, G. Bellussi and U. Romano, J. Catal. 129 (1991) 159–167 show moreover that the titanium-containing zeolite rapidly loses catalytic activity during its use as a catalyst for the epoxidation of propylene oxide. Clerici et al. describe two possible methods of regenerating the activity of the catalyst.

On the one hand the zeolite can be regenerated by calcining at 550° C., on the other hand the catalytic activity can be restored by washing with solvents at elevated temperature, preferably with methanol or with the solvent used for the epoxidation. Regeneration by calcining has the disadvantage that for this purpose the catalyst has first of all to be dried, then heated to the high calcining temperature and subsequently cooled again, which results in a considerable additional energy requirement and expenditure for apparatus. Regeneration by washing with a solvent is a slow process, which as a rule requires considerably more time than the actual epoxidation reaction.

An object of the invention therefore is to find a method for the regeneration of a titanium containing zeolite catalyst which can be carried out quickly and easily.

SUMMARY OF THE INVENTION

In achieving the above and other objects, one feature of the invention is a method for the regeneration of a catalyst, in particular a zeolite containing titanium atoms used as a catalyst for the preparation of epoxides from olefins and hydrogen peroxide, wherein the catalytic activity of the spent catalyst is regenerated by treatment with hydrogen peroxide in the absence of olefins and, thereafter, the regenerated catalyst is used again for the epoxidation of olefins.

DETAILED DESCRIPTION OF THE INVENTION

In accordance with the more detailed description of the invention, the epoxidation of an olefin, preferably of propylene, is carried out, as is described in EP 100 119, with preferably methanol being used as solvent. The zeolite catalyst containing titanium atoms which is used for the epoxidation, has its catalytic activity completely or partly exhausted during the reaction. Therefore, the catalyst is subsequently separated from the reaction mixture and optionally washed with a solvent, preferably with water. The spent catalyst is afterwards reacted with a solution of hydrogen peroxide in a solvent, preferably water.

In carrying out the method of this invention, the quantity of hydrogen peroxide is so chosen that it is more than ten times, preferably more than one hundred times, the quantity of olefin remaining in the catalyst and more than twice, preferably more than ten times, the quantity of titanium contained in the catalyst. The chosen concentration of the $H_2O_2$ solution used for the regeneration can be between 0.01 and 70 wt. %, preferably between 1 and 45 wt. %.

The regeneration process, as described, can be carried out at temperatures of between 0° and 200° C., preferably between 40° and 120° C. In a preferred embodiment of the invention the regeneration can be carried out at the boiling point of the aqueous $H_2O_2$ solution. The time necessary for the regeneration varies with the regeneration temperature applied and the concentration of $H_2O_2$ and can be so chosen that the required degree of regeneration is achieved.

Afterwards the catalyst is separated from the regenerating solution and optionally washed with a solvent, preferably water. It then can be returned to the epoxidation reaction.

If the solvent used in the regeneration is also used in the epoxidation reaction then the catalyst, without prior separation, can be returned to the epoxidation reaction together with the hydrogen peroxide solution used for the regeneration. If only a partial regeneration of the catalyst is required, the regeneration according to the invention can also be carried out in a way such that the quantity of catalyst separated from the reaction mixture is divided into two portions, only one of the portions is regenerated using hydrogen peroxide and the two portions are returned together or separately to the epoxidation reaction.

According to the invention the catalyst used can be titanium silicalite in the form of a suspension consisting alternatively of pure titanium silicalite, titanium silicalite containing a binder or titanium silicalite on an organic or inorganic supporting material. The epoxidation of the olefin, preferably of propylene, is carried out according to EP 100 119, with preferably methanol being used as solvent. Stirred-tank reactors, tubular loop reactors, bubble columns, continuous-flow reactors or other suitable reactors for suspensions, as well as combinations of these reactors, can be employed to carry out the epoxidation, with the selection Of the reactor type being made by the person skilled in the art appropriately to the reaction conditions selected and the olefin being epoxidized.

The catalyst is subsequently separated from the reaction mixture by filtration, centrifugation, decantation or other suitable method and washed with a solvent, preferably water. The catalyst can then again be suspended in an aqueous hydrogen peroxide solution having a concentration of between 0.01 and 70 wt. %, preferably between 1 and 45 wt. %, particularly preferably between 10 and 45 wt. %, and the suspension maintained at a temperature of between 0° and 150° C., preferably between 40° and 120° C. The contact time for the regeneration of the catalyst is so chosen that the required degree of regeneration, preferably between 20 and 100% of the initial catalytic activity, is achieved. The newly regenerated catalyst is subsequently returned to the epoxidation reaction, with the hydrogen peroxide solution used for the regeneration optionally being completely or partly separated. In the preferred use of aqueous hydrogen peroxide solutions having a hydrogen peroxide content of between 10 and 45 wt. % for the regeneration, the suspension of the catalyst in the regenerating solution can advantageously be passed to the epoxidation reaction without separation of the catalyst, so that the hydrogen peroxide not used for regeneration is utilized for epoxidizing the olefin.

In another preferred embodiment of the invention, for the epoxidation of the olefin a titanium silicalite shaped with a binder is used as a catalyst in the form of a fixed bed. In this case the catalyst packing is used for the epoxidation until the activity of the catalyst is completely or partly exhausted.

Thereafter, the catalyst packing is optionally washed with a solvent, preferably water. An aqueous hydrogen peroxide solution having a hydrogen peroxide content of between 0.01 and 70 wt. %, preferably between 1 and 40 wt. %, is then passed at a temperature of between 0° and 150° C., preferably between 40° and 120° C., over the catalyst packing until the required degree of regeneration is achieved. Here the hydrogen peroxide solution used for the regeneration can advantageously be circulated over the catalyst packing. Thereafter, the catalyst packing is used again for epoxidizing the olefin, optionally after intermediate washing with a solvent.

The method according to the invention for the preparation of epoxides from olefins and hydrogen peroxide using zeolite catalysts containing titanium atoms and the regeneration of the catalyst by treatment of the catalyst with hydrogen peroxide in the absence of the olefin, compared with the known prior art methods for the regeneration of the catalyst by calcining or by washing with solvents, has the advantage of an easier, quicker and distinctly better regeneration and return of the catalyst to the epoxidation reaction. It permits a more economical preparation of epoxides from olefins and hydrogen peroxide than do the known methods.

EXAMPLE 1

Determination of the catalytic activity of titanium silicalite in the epoxidation of propylene.

1 g of titanium silicalite in 300 ml of methanol is placed in H a thermostatted laboratory autoclave equipped with a gas dispersing stirrer at 40° C. under a propylene atmosphere and is saturated with propylene at an excess pressure of 3 bar. 12.9 g of 30 wt. % aqueous hydrogen peroxide solution is then added in one portion, with stirring, and the reaction mixture maintained at 40° C. and 3 bar, with further propylene being added via a pressure regulator in order to compensate for consumption owing to the reaction. At regular intervals samples are withdrawn through a filter and the hydrogen peroxide content of the reaction mixture is determined by redox titration with cerium(IV) sulphate solution. Plotting of in $(c/c_o)$ against the time t, with c being the measured $H_2O_2$ concentration at the time t and $c_o$ being the calculated $H_2O_2$ concentration at the start of the reaction, produces a straight line. The activity index k is determined from the gradient of this line by means of the relationship $$\frac{dc}{dt} = -k \cdot c \cdot c_{cat},$$

wherein $c_{cat}$ represents the concentration of catalyst in kg of catalyst per kg of reaction mixture. The activity index increases with increasing catalytic activity of the catalyst in the epoxidation of propylene.

EXAMPLE 2

Catalytic activity of fresh titanium silicalite

The activity of titanium silicalite, prepared according to the instructions in J.P.A. Martens et al., Appl. Catal. A99 (1993), 71–84, is examined as described in Example 1. An activity index of 18.9 $min^{-1}$ is determined.

EXAMPLE 3

Loss of activity of titanium silicalite through use as catalyst for the epoxidation of propylene 5 g of titanium silicalite, obtained as mentioned in Example 2, in 270 g of methanol is placed in laboratory H a thermostatted autoclave equipped with a gas dispersing stirrer at 40° C. under a propylene atmosphere and is saturated with propylene at an excess pressure of 3 bar. A mixture of 560g of 50 wt. % hydrogen peroxide and 3600 g of methanol is then added at a rate of 600 g/h, with stirring, and simultaneously the reaction mixture is withdrawn through a filter in a quantity such that the weight of the contents of the reactor remains constant. In the course of this the catalyst is retained in the reactor by the filter. During the metered addition of hydrogen peroxide, further propylene is added via a pressure regulator in order to maintain the pressure in the reactor constant. After 7 hours the metered addition of hydrogen peroxide is terminated, the catalyst is filtered off, washed with methanol at 20° C. and dried by exposure to air at 20° C. The activity of the spent catalyst is examined as in Example 1. An activity index of 1.3 $min^{-1}$ is determined. A repetition of the activity test according to Example 1 after 5 days produces an activity index of 1.7 $min^{-1}$. The activity indices established of 1.3 $min^{-1}$ and 1.7 $min^{-1}$ respectively show that titanium silicalite, when employed as catalyst for the epoxidation of propylene using hydrogen peroxide, largely loses its catalytic activity in this reaction and does not recover its catalytic activity without measures for regeneration being taken.

EXAMPLE 4 AND 5 (COMPARATIVE EXAMPLES)

Regeneration of spent titanium silicalite by boiling with methanol or water

EXAMPLE 4

1 g of spent titanium silicalite catalyst from Example 3 is heated under reflux for 4 h in 25 ml of methanol and then filtered. The catalytic activity is examined as in Example 1. An activity index of 1.3 $min^{-1}$ is determined.

EXAMPLE 5

1 g of spent titanium silicalite catalyst from Example 3 is heated under reflux for 4 h in 25 ml of demineralized (distilled) water, subsequently filtered and then washed with methanol. The catalytic activity is examined as in Example 1. An activity index of 1.6 $min^{-1}$ is determined.

Examples 4 and 5 show that a regeneration of spent titanium silicalite by boiling respectively with methanol at 65° C. and with water at 100° C. for a period of 4 h brings about no appreciable improvement in the catalytic activity.

EXAMPLES 6–8 (according to the invention)

Regeneration of spent titanium silicalite by boiling with hydrogen peroxide

EXAMPLE 6

1 g of spent titanium silicalite catalyst from Example 1 is heated under reflux for 4 h in 25 ml of 5 wt. % of aqueous hydrogen peroxide solution, subsequently filtered and then washed with water and methanol. The catalytic activity is examined as in Example 1. An activity index of 18.3 $min^{-1}$ is determined. Thus, it is noted that the activity index has been restored to be essentially the same as that of the catalyst before the epoxidation reaction.

EXAMPLE 7

Example 6 is repeated, with the treatment using hydrogen peroxide being shortened to 1 h. An activity index of 11.2 $min^{-1}$ is determined.

EXAMPLE 8

Example 6 is repeated, with the treatment using hydrogen peroxide being shortened to 15 min. An activity index of 4.9 min$^{-1}$ is determined.

Examples 6–8 show that spent titanium silicalite can be completely regenerated by a treatment according to the invention using 5 wt. % of hydrogen peroxide at 100° C. for a period of 4 h and that, by selecting the duration of treatment using hydrogen peroxide, a specific partial regeneration of the catalyst can be achieved.

Thus, depending on the degree of regeneration desired, typical times for contacting the spent catalyst range from about 15 minutes to 4 hours. Temperature conditions can vary, but at 100° C. the above times are suitable. At lower temperatures correspondingly longer times can be used.

Further variations and modifications of the foregoing will be apparent to those skilled in the art and are intended to be encompassed by the claims appended hereto.

German priority application 195 28 220.5 is relied on and incorporated herein by reference.

I claim:

1. A method for the regeneration of a catalyst which is a zeolite containing titanium atoms that is used as a catalyst for the reaction for the preparation of epoxides from olefins and hydrogen peroxide, comprising:

treating said catalyst after the catalytic activity of the catalyst is at least partially exhausted at a sufficient temperature and for a sufficient period of time to regenerate said catalyst with hydrogen peroxide in the absence of olefin.

2. The method according to claim 1, wherein the catalyst is regenerated by treating with an aqueous hydrogen peroxide solution which contains between 0.01 and 70 wt. % of hydrogen peroxide.

3. The method according to claim 2, wherein the catalyst is regenerated by treating with an aqueous hydrogen peroxide solution which contains between 1 and 45 wt. % of hydrogen peroxide.

4. The method according to claim 1, wherein said treating is carried out at a temperature of between 0° and 200° C.

5. The method according to claim 4, wherein said treating is carried out at a temperature of between 40° and 120° C.

6. The method according to claim 1, further comprising returning said catalyst after regeneration to said reaction for epoxidation of olefins.

7. A method for the preparation of an epoxide comprising reacting an olefin with hydrogen peroxide in the presence of a zeolite containing titanium atoms as catalyst to thereby obtain an epoxidation of said olefin, and wherein the catalytic activity of the catalyst declines, regenerating said catalyst by treating said catalyst with hydrogen peroxide in the absence of said olefin to thereby obtain the regenerated catalyst.

8. The method according to claim 7, wherein said olefin is propylene.

9. The method according to claim 7, wherein said epoxidation is carried out in a mixture of methanol and water as solvent.

10. The method according to claim 7, wherein said catalyst is in the form of a suspension.

11. The method according to claim 7, wherein the catalyst is regenerated by treating with an aqueous hydrogen peroxide solution which contains between 10 and 45 wt. % of hydrogen peroxide, and the mixture of catalyst and hydrogen peroxide from the regeneration is used in the epoxidation reaction without prior separation.

12. The method according to claim 7, wherein said catalyst is in the form of a fixed bed.

13. The method according to claim 7, further comprising circulating the hydrogen peroxide solution over the fixed bed during the regeneration.

14. The method according to claim 8, wherein said epoxidation is carried out in a mixture of methanol and water as solvent.

15. The method according to claim 8, wherein said catalyst is in the form of a suspension.

16. The method according to claim 9, wherein said catalyst is in the form of a suspension.

17. The method according to claim 8, wherein the catalyst is regenerated by treating with an aqueous hydrogen peroxide solution which contains between 10 and 45 wt. % of hydrogen peroxide, and the mixture of catalyst and hydrogen peroxide from the regeneration is used in the epoxidation reaction without prior separation.

18. The method according to claim 9, wherein the catalyst is regenerated by treating with an aqueous hydrogen peroxide solution which contains between 10 and 45 wt. % of hydrogen peroxide, and the mixture of catalyst and hydrogen peroxide from the regeneration is used in the epoxidation reaction without prior separation.

19. The method according to claim 10, wherein the catalyst is regenerated by treating with an aqueous hydrogen peroxide solution which contains between 10 and 45 wt. % of hydrogen peroxide, and the mixture of catalyst and hydrogen peroxide from the regeneration is used in the epoxidation reaction without prior separation.

20. The method according to claim 1, wherein said treating is carried out by heating said catalyst under reflux for 15 minutes to 4 hours.

21. The method according to claim 1, wherein said treating is carried out at a sufficient temperature and for a sufficient period of time to achieve an activity index essentially the same as that of the catalyst before said reaction.

* * * * *